United States Patent [19]

North

[11] Patent Number: 5,502,220
[45] Date of Patent: Mar. 26, 1996

[54] PROCESS FOR THE PREPARATION OF INTERMEDIATES USEFUL IN THE PREPARATION OF PYRANYL CYANOGUANIDINE DERIVATIVES

[75] Inventor: Jeffrey T. North, Trenton, N.J.

[73] Assignee: Bristol-Myers Squibb Company, Princeton, N.J.

[21] Appl. No.: 362,711

[22] Filed: Dec. 23, 1994

Related U.S. Application Data

[63] Continuation of Ser. No. 80,046, Jun. 18, 1993, abandoned.

[51] Int. Cl.$^6$ .................. C07D 311/60; C07D 491/052
[52] U.S. Cl. .............................................. 549/396; 546/115
[58] Field of Search .................................. 514/302, 456; 546/115; 549/396

[56] References Cited

U.S. PATENT DOCUMENTS

| | | | |
|---|---|---|---|
| 4,315,862 | 2/1982 | Elsohly et al. | 549/408 |
| 5,140,031 | 8/1992 | Atwal | 514/302 |
| 5,232,944 | 8/1993 | Gericke | 514/456 |

FOREIGN PATENT DOCUMENTS 0462761  12/1991  European Pat. Off. .

OTHER PUBLICATIONS

Camps, "Fluorinated Chromenes . . . ", *J. Heterocyclic Chem.* vol. 17, p. 1377, 1980.
Bandaianayake, "3-Hydroxy—. . . ", *J. Chem. Soc.*, pp. 811–816, 1971.
G. P. Ellis, "Chromenes, Chromanones, and Chromones", J. Wiley & Sons, pp. 47–49, vol. 31, No. 130, 1977.
W. Hoepfner et al., "Syntheseund Riechstoff-Eigenschaften von Rosenoxid-Analoga", *Liebigs Ann. Chem.*, 1986, pp. 99–113.
G. Aslani-Shotorbani et al., "The Isopropylidenation Of D-Ribose Diethyl Dithioacetal And Ribitol. A New Synthesis Of a-And b-D-Ribofuranosylethyne via 2,3:4,5-DI-O--Isopropylidene-aldehydro-D-Ribo", *Carbohydrate Research*, 136, 1985, pp. 37–52.
W. M. Bandaranayake et al., "3-Hydroxy-3-methyl-1, 1-dimethyoxybutane, a New Reagent for Dimethyl--chromenylation: Synthesis of Lonchocarpin, Jacareubin, Evodionol Methyl Ether, and other Chromens", *J. Chem. Soc (C), 1971, pp. 811–816.*
D. G. Clarke et al., "Conversion of Phenols into Chromens: Regiospecificity and Scope", *J. C. S. Perkins 1, pp. 1007–1015, 1974.*
F. Camps et al., "Fluorinated Chromenes, III. Synthesis of 3-Fluoro-2,2-dimethyl-2H-chromenes", *J. Heterocyclic Chem.*, 17, 1377 (1980) pp. 1377–1379.

*Primary Examiner*—C. Warren Ivy
*Assistant Examiner*—D. Margaret M. Mach
*Attorney, Agent, or Firm*—Ellen K. Park

[57] ABSTRACT

A process for preparing compounds of the formula

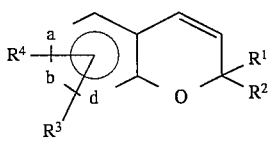

I where a, b d, $R^1$, $R^2$, $R^3$ and $R^4$ are as defined herein including condensation of a phenol of formula

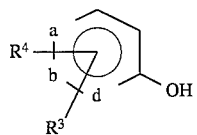

II with an acetal of formula

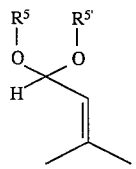

III in the presence of a catalytic amount of a tertiary amine. The compounds of formula I are intermediates useful in the preparation of pyranyl cyanoguanidine derivatives.

5 Claims, No Drawings

PROCESS FOR THE PREPARATION OF INTERMEDIATES USEFUL IN THE PREPARATION OF PYRANYL CYANOGUANIDINE DERIVATIVES

This is a continuation of application Ser. No. 08/080,046, filed Jun. 18, 1993 now abandoned.

FIELD OF THE INVENTION

The present invention relates to novel processes for preparing intermediates useful in preparing compounds having potassium channel activating activity.

BRIEF DESCRIPTION OF THE INVENTION

The present invention is directed to a novel process for preparing compounds of the formula

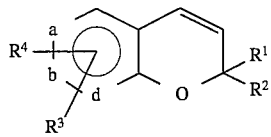

As used in formula I, and throughout the specification, the symbols have the following meanings:

a, b, and d are all carbon atoms or one of a, b and d is a nitrogen atom or -NO- and the others are carbon atoms;

$R^1$ and $R^2$ are independently hydrogen, alkyl or arylalkyl, or, $R^1$ and $R^2$ taken together with the carbon atom to which they are attached form a 5- to 7-membered carbocyclic ring;

$R^3$ is hydrogen, alkyl, haloalkyl, alkenyl, alkynyl, cycloalkyl, arylalkyl, cycloalkylalkyl, -CN, -NO$_2$, -COR, -COOR, -CONHR, -CONRR', -CF$_3$, S-alkyl, -SOalkyl, -SO$_2$alkyl,

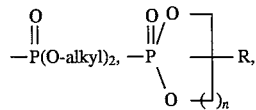

R, halogen, amino substituted amino, -OH, -O-alkyl, -OCF$_3$, -OCH$_2$CF$_3$, -OCOalkyl, -OCONRalkyl, -NRCOalkyl, -NRCOOalkyl or -NRCONRR' wherein R and R' in the above groups is independently hydrogen, alkyl, haloalkyl, aryl, arylalkyl, cycloalkyl, or (cycloalkyl)alkyl;

$R^4$ is hydrogen, alkyl, -OH, -O-alkyl, amino substituted amino, -NHCOR, -CN or -NO$_2$; and n is an integer of 1 to 3.

Compounds of formula I may be prepared by condensation of a phenol of formula

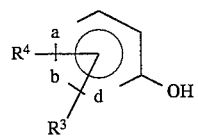

with an acetal of formula

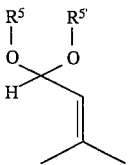

where $R^5$ and $R^{5'}$ are the same alkyl groups or can together form a dioxolane ring, in the presence of a catalytic amount of a tertiary amine in an inert organic solvent such as toluene or xylene to form compounds of formula I.

DESCRIPTION OF THE INVENTION

The present invention relates to novel processes for preparing compounds of formula I. Listed below are definitions of various terms used to describe the compounds of the instant invention. These definitions apply to the terms as they are used throughout the specification (unless they are otherwise limited in specific instances) either individually or as part of a larger group.

The term "alkyl" refers to straight and branched chain hydrocarbons, containing 1 to 8 carbons in the normal chain, preferably 1 to 5 carbons such as methyl, ethyl, propyl, butyl, pentyl, the various branched chain isomers thereof such as isopropyl, t-butyl, isobutyl, 4,4-dimethylpentyl, 2,2, 4-trimethylpentyl and the like as well as such groups including a halo-substituent, such as F, Br, Cl or I such as CCl$_3$ or CF$_3$, an alkoxy substituent, an aryl substituent, an alkyl-aryl substituent, a haloaryl substituent, a cycloalkyl substituent, an alkyl-cycloalkyl substituent, a hydroxy substituent, an alkylamino substituent, an alkanoylamino substituent, an arylcarbonylamino substituent, a nitro substituent, a cyano substituent, a thiol substituent or an alkylthio substituent.

The terms "alkoxy" and "alkylthio" refer to such alkyl groups as described above linked to an oxygen atom or sulfur atom respectively.

The term "alkenyl" refers to such groups as described above for alkyl, further containing at least one carbon to carbon triple bond.

The term "cycloalkyl" as employed herein includes saturated cyclic hydrocarbon groups containing 3 to 7 ring carbons with cyclopropyl, cyclopentyl and cyclohexyl being preferred.

The term "halogen" or "halo" refers to chlorine, bromine, iodine or fluorine.

The term "aryl" refers to phenyl, 1-naphthyl, 2-naphthyl; or mono substituted phenyl, 1-naphthyl, 2-naphthyl wherein said substituent is alkyl of 1 to 4 carbons, alkylthio of 1 to 4 carbons, alkoxy of 1 to 4 carbons, halo, nitro, cyano, hydroxy, amino, -NH-alkyl wherein alkyl is of 1 to 4 carbons, -N(alkyl)$_2$ wherein alkyl is of 1 to 4 carbons,

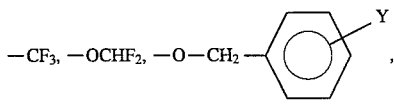

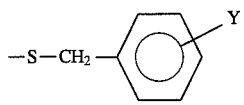

(wherein Y is hydrogen, alkyl of 1 to 4 carbons, alkoxy of 1 to 4 carbons, alkylthio of 1 to 4 carbons, halo, hydroxy or -CF$_3$), -O-CH$_2$-cycloalkyl, or -S-CH$_2$-cycloalkyl; or di-substituted phenyl, 1-naphthyl, 2-naphthyl wherein said substituents are selected from methyl, methoxy, methylthio, halo, -CF$_3$, nitro, amino, and -OCHF$_2$. Preferred aryl groups include unsubstituted phenyl and monosubstituted phenyl wherein the substituent is nitro, halo, -CF$_3$, alkyl, cyano or methoxy.

The term "heterocyclo" or "hetero" refers to fully saturated or unsaturated rings of 5 or 6 atoms containing one or two oxygen and sulphur atoms and/or one to four nitrogen atoms provided that the total number of hetero atoms in the ring is 4 or less. The hetero ring is attached by way of an available carbon atom. Preferred monocyclic hetero groups include 2- and 3-thienyl, 2- and 3-furyl, 2-, 3- and 4-pyridyl, and imidazolyl. The term hetero also includes bicyclic rings wherein the five or six membered ring containing oxygen, sulphur and nitrogen atoms as defined above is fused to a benzene ring and the bicyclic ring is attached by way of an available carbon atom. Preferred bicyclic hetero groups include 4, 5, 6, or 7-indolyl, 4, 5, 6 or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5,6 or 7-benzimidazolyl, 4, 5, 6 or 7-benzoxadiazolyl and 4, 5, 6 or 7-benzofuranzanyl.

The term heterocyclo also includes such monocyclic and bicyclic rings wherein an available carbon atom is substituted with an alkyl of 1 to 4 carbons, alkylthio of 1 to 4 carbons, alkoxy of 1 to 4 carbons, halo, nitro, keto, cyano, hydroxy, amino, -NH-alkyl wherein alkyl is of 1 to 4 carbons, -N(alkyl)$_2$ wherein alkyl is of 1 to 4 carbons, -CF$_3$, OCHF$_2$ or such monocyclic and bicyclic rings wherein two or three available carbons have substituents selected from methyl, methoxy, methylthio, halo, -CF$_3$, nitro, hydroxy, amino and -OCHF$_2$.

The term "substituted amino" refers to a group of the formula -NZ$^1$Z$^2$ wherein Z$^1$ is hydrogen, alkyl, cycloalkyl, aryl, arylalkyl, (cycloalkyl)alkyl and Z$^2$ is alkyl, cycloalkyl, aryl, arylalkyl, (cycloalkyl)alkyl or Z$^1$ and Z$^2$ taken together with the nitrogen atom to which they are attached are 1-pyrrolidinyl, 1-piperindinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperindinyl or 1-azepinyl substituted with alkyl, alkoxy, alkylthio, halo, trifluoromethyl or hydroxy.

Compounds of formula I may be prepared by condensation of a phenol of formula

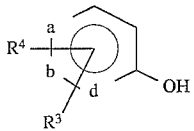

II with an acetal of formula

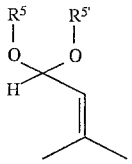

III where R$^5$ and R$^{5'}$ are the same alkyl group or can together form a dioxolane ring, in the presence of a catalytic amount of a tertiary amine such as a quinoline, N-methylmorpholine, 4-dimethylaminopyridine, 1,4-diazabicyclo[2.2.2]octane, 1,8-diazabicyclo[5.4.0]undec-7-ene, tributylamine, picoline, lutidine, preferably pyridine or 3-picoline in an inert organic solvent such as toluene or xylene preferably at a temperature between about 90° C. to about 150° C. to form compounds of formula I. It is preferred that R$^5$ and R$^{5'}$ are ethyl.

In preparing compounds of formula I as described above, it may be necessary to protect any amine, hydroxy or thiol groups during the reaction with protecting groups as known in the art.

Compounds of formula II are commercially available or are readily prepared by methods known in the art.

Compounds of formula III may be prepared by methods disclosed in the literature. For example, W. Hoepfrer et al., *Liebigs, Ann. Chem.*, 99 (1986). Also see J. R. Hwu et al., *J. Org. Chem.*, 52, 188 (1987).

In addition, compounds of formula III were R$^4$ and R$^{5'}$ are alkyl may be prepared by the novel process of treating compounds of formula

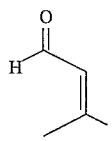

IV with an alcohol R$^5$OH (where R$^5$ is alkyl) and with an acidic catalyst such as sodium hydrogen sulfate, potassium hydrogen sulfate or quaternary ammonium hydrogen sulfate and a dehydrating agent such as a compound of formula HC(OR$^5$)$_3$.

Compounds of formula I are key intermediates in the preparation of pyranyl cyanoguanidine derivatives of the formula

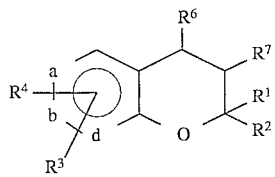

V where a, b, d, R$^1$, R$^2$, R$^3$, and R$^4$ are as defined for formula I and
R$^6$ is

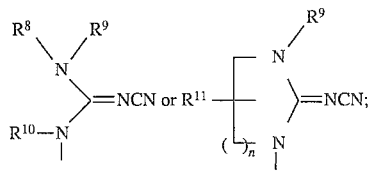

R$^7$ is hydrogen, hydroxy or

R$^8$ and R$^9$ are independently hydrogen, alkyl, alkenyl, aryl, (heterocyclo)alkyl, heterocyclo, arylalkyl, cycloalkyl, (cycloalkyl)alkyl or substituted alkyl wherein the substituents are alkoxy, alkylthio and substituted amino; or R$^8$ and R$^9$ taken together with the nitrogen atom to which they are attached from 1-pyrrolidinyl, 1-piperidinyl, 1-azepinyl, 4-morpholinyl, 4-thiamorphilinyl, 1-piperazinyl, 4-alkyl-1-piperazinyl or 4-arylalkyl-1-piperazinyl, wherein each of the so-formed groups can be substituted with alkyl, alkoxy, alkylthio, halogen or trifluoromethyl; and R$^{10}$ and R$^{11}$ are independently hydrogen, alkyl, alkenyl, aryl, arylalkyl, cycloalkyl or (cycloalkyl)alkyl; or R$^{11}$ can be an aryl group fused to 2-carbon atoms of the cyanoguanidine ring portion.

Compounds of formula V and methods of preparing such compounds are disclosed in U.S. Pat. No. 5,140,031, the disclosure of which is incorporated by reference herein.

Preferred compounds of formula V are those where $R^6$ is

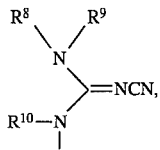

5 and $R^8$ is mono- or di-substituted phenyl.

An exemplary method of preparing the compounds of formula V where $R^6$ is

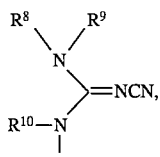

using the intermediates of formula I, prepared as disclosed herein includes reacting compounds of formula I with an oxidizing agent such as commercial bleach using a metal catalyst such as a chiral manganese catalyst of the formula

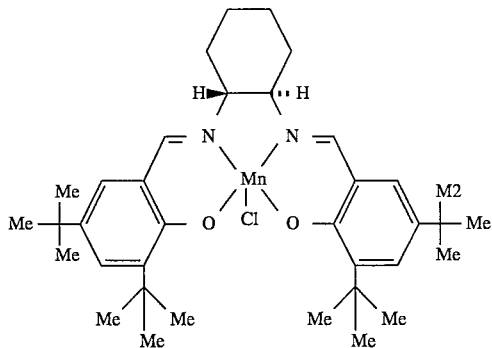

VI as described by E. Jacobsen, et al. (*Tetrahedron Letters,* 32, 5055–5058 (1991), optionally in the presence of 4-phenylpyridine N-oxide, to provide an epoxide of formula

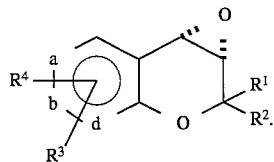

VII

The epoxides of formula VII may then be treated with an amine such as ammonia to provide the amine of formula

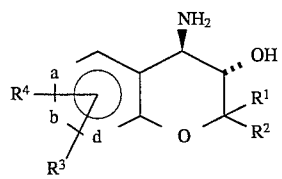

VIII which may then be converted to the methanesulfonate salt and then treated with an isocyanide dihalide of the formula

$R^9\text{-N}=C(X)_2$  IX (where $R^9$ is other than hydrogen and X is a halogen, preferably chlorine) in solvent such as dichloromethane, 1,2-dichloroethane, acetonitrile, ethyl acetate or preferably an alcoholic solvent such as isopropyl alcohol or ethanol, containing a tertiary amine such as diisopropylethylamine to form a compound of formula

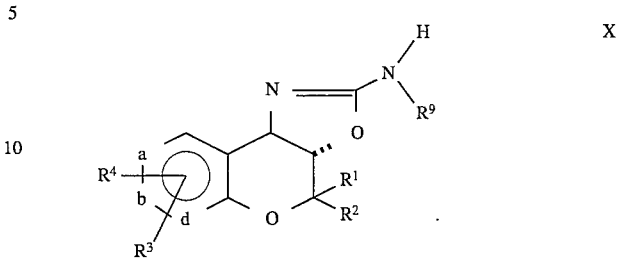

X

Alternatively treatment of compounds of formula VIII with an isothiocyanate of the formula

$R^9\text{-N}=C=S$   XI such as 4-chlorophenylisothiocyanate provides a thiourea of formula

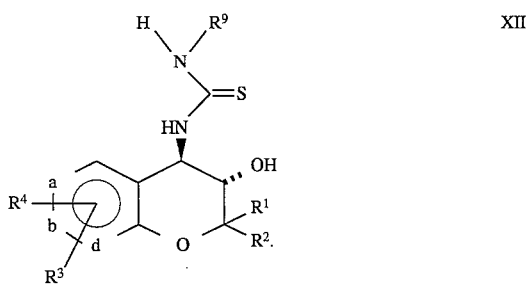

XII

Subsequent treatment of the thiourea of formula XII with a carbodiimide such as 1-ethyl-3-(3-dimethylaminopropyl-)carbodiimide hydrochloride provides the compounds of formula X.

Treatment of compounds of formula X with cyanamide in a solvent such as alcohol or acetonitrile, optionally in the presence of a base such as triethylamine or 2,6-lutidine provides the compounds of formula V where $R^7$ is hydroxy. Compounds of formula V where $R^7$ is hydrogen may be prepared by dehydration of the compounds of formula V where $R^7$ is hydroxy, followed by reduction by procedures known in the art.

Preferred compounds of formula IX include substituted alkyl and aryl isocyanide dihalides such as substituted phenyl isocyanide dichlorides. The most preferred compounds of formula IX is 4-chlorophenyl isocyanide dichloride. Substituted alkyl and aryl isocyanide dihalides are known (E. Kühle, "Carbonic Acid Derivatives from Formamides", *Angew, Chem. Int. Ed.,* (1962), 1,647–652; D. Ferchland et al., "process for the Preparation of Aryl Isocyanide-Dichlorides", U.S. Pat. No. 4,401,603; and E. Kühle et al., "New Methods of Preparative Organic Chemistry-reactions of Isocyanide Dihalides and their Derivatives", *Angew, Chem. Int. Ed.,* (1969), 8, 20–34).

The following examples and preparations describe the manner and process of making and using the preferred embodiments of the invention and are illustrative rather than limiting. It should be understood that there may be other embodiments which fall within the spirit and scope of the invention as defined by the claims appended hereto.

EXAMPLE 1

2,2-Dimethyl-2H-1-benzopyran-6-carbonitrile

A. 1,1-Diethoxy-3-methyl-2-butene

Under an argon atmosphere, a 250-mL, round-bottomed flask equipped with a stir bar was charged with abs. ethanol (52 mL, 892 mmol, 5.0 eq). The flask was cooled to 4° C. (internal) in an ice bath. Triethyl orthoformate (29.7 mL, 178 mmol, 1.0 eq) was added followed by 3-methyl-2-butenal (17.2 mL, 178 mmol, 1.0 eq). The resulting clear, colorless solution was further cooled to 2° C. (internal). Potassium hydrogen sulfate (1.277 g, 9.38 mmol, 0.05 eq) was then added in one portion, resulting in an immediate exotherm to 10° C. The heterogeneous mixture was allowed to warm to 21° C. (internal) over 45 minutes (within 20 minutes, the mixture became slightly cloudy) and then stirred for an additional 15 minutes. The reaction mixture was then filtered and the remaining solid rinsed with abs. ethanol (5 mL). To the resulting clear, colorless solution was added anhydrous potassium carbonate (2.615 g, 18.92 mmol). The mixture was stirred for one hour before filtering off the potassium carbonate. The solid was rinsed with abs. ethanol (5 mL) and the filtrate was vacuum distilled (172 mm Hg) through a Vigereux column (13.5 cm) to produce 24.14 g (85% yield) of the title compound (boiling point 115°–119° C.).

B. 2,2-Dimethyl-2H-1-benzopyran-6-carbonitrile

A 500-mL, 3-necked, round-bottomed flask topped with a distilling head, internal temperature probe/argon inlet, and an overhead stirrer was sequentially charged with the title A compound, 1,1-diethoxy-3-methyl-2-butene (26.59 g, 168.00 mmol), p-xylene (300 mL), 4-cyanophenol (15.00 g, 125.92 mmol), and 3-picoline (3.0 mL, 2.870 g, 30.83 mmol). The reaction mixture was rapidly stirred. The internal temperature was rapidly brought up to 115° C. and then slowly raised in order to distill off the ethanol formed during the reaction.

After 24 hours the reaction mixture was a clear, golden yellow solution. The distillate collected was a clear, colorless liquid (4.96 g) and was determined to be ~98% ethanol and ~2% p-xylene by $^1$H NMR analysis. The reaction was cooled to room temperature, poured into a mixture of ethyl acetate (150 mL) and 1N hydrochloric acid (400 mL), and after mixing vigorously the layers were separated. The organic phase was washed again with 1N hydrochloric acid (200 mL). The acidic, aqueous layers were combined and extracted with ethyl acetate (100 mL). The organic solutions were combined and washed with 1N sodium hydroxide (1×400 mL, 1×200 mL). The basic, aqueous layers were combined and extracted with ethyl acetate (100 mL). The organic solutions were combined, washed with saturated sodium chloride solution (300 mL), dried (magnesium sulfate), filtered, and concentrated to a golden yellow liquid that contained a small amount of solid (20.85 g, 89% crude yield).

To a portion of this material (20.22 g) was added hexanes (20.0 mL). The very cloudy, yellow mixture was heated to a reflux (hazy, yellow), cooled to room temperature, seeded, and then allowed to stand undisturbed for nine hours. The mixture was then cooled to, and maintained at, 5° C. for 14 hours. The supernatant liquor was decanted and filtered. The crystals were removed, placed atop the same filter, and washed quickly with 0° C. hexanes (1×6 mL, 2×7 mL). The crystals were air-dried (30 minutes), then placed under high vacuum (<1 mm Hg until a constant weight was attained) to yield the products as off-white crystals (14.91 g).

EXAMPLE 2

2,2-Dimethyl-2H-1-benzopyran-6-carbonitrile

In a dried 250-mL flask, trimethylsilyl trifluoromethanesulfonate (TMSOTf) (0.20 mL, 1 mmol) was added to methylene chloride at −78° C. under argon, followed by 1,2-bis(trimethylsilyloxy)ethane (BTSE) (30.5 mL, 125 mmole) and 3-methyl-2-butenal (10 mL, 104 mmole). The resulting bright yellow solution was stirred at −78° C. for 3.3 hours. Over time, the solution became orange. The reaction was terminated by adding triethylamine (7.2 mL, 52 mmole). The resulting yellow-tinted solution was transferred into a separatory funnel containing saturated sodium bicarbonate solution (150 mL). The organic layer was collected and the aqueous layer was extracted; with methylene chloride (1×50 mL). The organic layers were combined, washed with brine (1×100 mL), dried over magnesium sulfate, and concentrated in vacuo to give a yellow oil (17.37 g).

The solid was dissolved in methanol (74 mL) and cooled to 0° C. Potassium carbonate (0.119 g, 0.86 mmole) was added under argon and the mixture stirred; at 0° C. for 1.5 hours. The mixture was concentrated in vacuo and the residue diluted with ethyl acetate (20 mL). The resulting solution was washed with brine (1×65 mL). The organic layer was collected, dried over magnesium sulfate and concentrated in vacuo to 11.3 g of a yellow oil. Vacuum distillation (Vigereux column. 76°–80° C., 24–26 mm) gave the desired dioxolane as a clear colorless oil (9.0 g, 68%).

Under an argon atmosphere, 4-cyanophenol (0.186 g, 1.56 mmole), p-xylene (1 mL), the dioxolane prepared above (0.2 g, 1.56 mmole), and pyridine (0.12 mL, 1.56 mmole) were combined in that order. The mixture was heated to 140° C. (internal temperature). After 24 hours, the reaction mixture was diluted with ethyl acetate (3 mL) and washed with 10% hydrochloric acid. The organic layers were collected, washed with 1N sodium hydroxide, brine, dried over magnesium sulfate, and concentrated in vacuo to give the title compound as a dark brown oil (0.085 g, 30% yield).

EXAMPLE 3

(3S-trans)-N-(4-Chlorophenyl)-N"-cyano-N'-(6-cyano-3,4-dihydro-3-hydroxy-2,2-dimethyl-2H-1-benzopyran-4-yl)guanidine A. (1aS-cis)-1a,7b-Dihydro-2,2-dimethyl-2H-oxireno[c][1]-benzopyran-6-carbonitrile A buffered solution of NaOCl (110.70 mmol, 205 mL of a 0.54 M solution was cooled to an internal temperature of 1° C. The pH of a freshly prepared bulk solution of Clorox® bleach (250 mL from a freshly opened bottle; 5.25% aq. NaOCl, 0.757 M NaOCl) and 0.05 M Na$_2$HPO$_4$ (100 mL) was adjusted from ~10.3 to 11.30 with 1 N sodium hydroxide (the buffered solution should be used within 30 minutes of preparation). A second flask was sequentially charged with the title compound of Example 1 (10.053 g, 54.27 mmol), methylene chloride (50 mL), ((1S-trans)-chloro[2,2'-[1,2-cyclohexanediylbis(iminomethyl)]bis[4,6-bis(1,1-dimethylethyl)phenolato-N,N',O,O']] manganese) (0.378 g, 0.54 mmol) and 4-phenylpyridine N-oxide (94 mg, 0.55 mmol). After stirring for ~five minutes at room temperature, the solution was cooled to 0° C., then added to the rapidly stirred (overhead stirrer) NaOCl solution. The black heterogeneous mixture was vigorously stirred at 0° C. At various times aliquots were removed from the organic phase and used to determine the percent conversion by GC analysis. After stirring for 22 hours at 0° C. to 5° C., the reaction was complete by GC analysis. The brown heterogeneous reaction mixture was filtered through Celite 545®. The brown residue left on the filter pad was washed with methylene chloride (~300 mL). The filtrates were combined, the layers were separated, and the aqueous layer was extracted with methylene chloride (~50 mL). The organic solutions were combined, washed with saturated sodium chloride solution (1× 300 mL), dried (sodium sulfate), filtered, and concentrated to a yellow solid (11.219 g, 94.00% e.e. by chiral GC analysis).

A portion of this material (10.712 g) was slurried in isopropanol (31 mL). After stirring for four hours, the solid was isolated via filtration, washed with isopropanol (3×10 mL), air-dried (15 minutes), and dried under high vacuum (3.5 hours at <1 mm Hg) to yield 8.873 G of the title compound as a white solid (22 99.9% e.e. by chiral GC analysis). $[\alpha]_D = -89.2°$ (c=1.02, MeOH).

B. (3S-trans)-4-Amino-3,4-dihydro-3-hydroxy-2,2-dimethyl- 2H-pyran-6-carbonitrile, methanesulfonate salt The title A compound (8.0 g, 39.8 mmol) was weighed into a 500-mL, 3-necked flask equipped with a water condenser, temperature probe and gas dispersion tube. A 1:1 mixture of ethanol (190 proof, 80 mL) and concentrated ammonium hydroxide (80 mL) was added and the slurry was stirred in an oil bath and heated to an internal temperature of 50° C. while sparging with $NH_3$ gas. The initial pH of the reaction mixture at this temperature was 12.25 and the slurry gradually dissolved into a clear yellow solution. The reaction mixture was continuously sparged with $NH_3$ gas and the pH remained at ~12.2–12.1 during the course of the reaction. After five hours, >95% of the starting epoxide was consumed by TLC. The reaction was cooled and sparged with $N_2$ to remove $NH_3$ (~45 minutes) and then concentrated in vacuo to remove $NH_3$ and ethanol. The remaining aqueous mixture (pH 9) was cooled to 0° C., diluted with ethyl acetate (80 mL) and the pH was raised to 10.4 with 4N sodium hydroxide (~3.5 mL). The resulting yellow solution was transferred to a separatory funnel and additional ethyl acetate (75 mL) and water (75 mL) were added to achieve phase separation. The mixture was shaken and the layers were separated. The aqueous layer was extracted with additional ethyl acetate (4× 75 mL). The combined ethyl acetate extracts were washed with brine, dried (magnesium sulfate), filtered and concentrated in vacuo. Hexane was added to the resulting oil. Evaporation followed by drying under high vacuum produced 9.15 g (100% yield, corrected for residual solvents) of crude amine as a white foam.

The amine (8.95 g) was slurried in acetonitrile (89 mL) under argon in a 250-mL, 3-necked flask equipped with a mechanical stirrer, temperature probe and water condenser. The suspension was heated to an internal temperature of 62° C. at which point most of the solids dissolved. Methanesulfonic acid (41.8 mmol, 2.71 mL) was added slowly over ten minutes such that the internal temperature was maintained at 62° C. to 70° C. The resulting crystal slurry was stirred at 62° C. for one hour, then slowly cooled to room temperature and stirred overnight. The white crystals were filtered using fresh acetonitrile (20 mL) to aid in the transfer. The product was washed with additional acetonitrile (2×20 mL) and hexane (2× 20 mL) and dried in vacuo to a constant weight of 11.05 g (90% yield from the title A compound).

C. (3S-trans)-2-[(4-Chlorophenyl)amino]-3α-,4,9β-trihydro- 4,4-dimethyl-2H-[1]benzopyrano[4,3-d]-oxazole-8-carbonitrile To a solution of the title B compound (1.0 g, 3.18 mmol) in absolute ethanol (5 mL) at room temperature under argon, was added diisopropylethylamine (2.40 mL, 13.78 mmol, 4.33 eq). To the resulting solution was added 4-chlorophenyl isocyanide dichloride (1.0 g, 4.80 mmol, 1.50 eq). After heating at 43° C. for 24 hours, the resulting mixture was diluted with toluene (~80 mL) and washed with water, 5% aqueous $NaHSO_4$ (25 mL), 1N $HaHCO_3$, and brine. After drying (magnesium sulfate), the solvent was removed in vacuo to give a light yellow solid. This solid was then slurried with heptane (10 mL). The solid was collected by filtration, washed with heptane, and dried to give the crude product (1.14 g, HPLC HI=94.0%). HI is an estimate of the purity of a sample and is calculated from the peak area of the main component relative to the total peak area of all components of the sample. This crude product (1.097 g) was recrystallized from ethyl acetate (3 mL) and heptane (5 mL) to give the product as a colorless solid: 754 mg (69%); HPLC HI=99.5%;

$[\alpha]_D = -106.9°$ (c=0.55, $CH_3OH$).

D. (3S-trans)-N-(4-Chlorophenyl)-N''-cyano-N'-(6-cyano- 3,4-dihydro-3-hydroxy-2,2-dimethyl-2H-1-benzopyran- 4-yl)guanidine A mixture of the title C compound (4.00 g) and cyanamide (1.42 g) in isopropanol (22 mL) was prepared under argon in a 100-mL flask equipped with a magnetic stirrer and a condenser. An amount of 2,6-lutidine (1.28 g) was added and the mixture heated in a 95° C. bath to give a clear colorless solution. The solution was heated for 16 hours in the 95° C. bath and monitored by HPLC. The solution was diluted with ethyl acetate (150 mL) was washed with water (50 mL) containing 1N hydrochloric acid (14 mL). The ethyl acetate solution was diluted with ethyl acetate (25 mL) and washed with 5:2 water-brine (70 mL), and then saturated sodium bicarbonate and brine. The organic layer was dried over magnesium sulfate, filtered, and concentrated in vacuo to give an off-white amorphous solid, 4.91 g with HPLC HI=97.8%. This material was dissolved in hot 95% ethanol (60 mL) diluted with hot water (62 mL) and stirred in a 63° C. bath for four hours as a white solid precipitated. The mixture was allowed to stir at room temperature overnight. The mixture was filtered and the solid was washed with water (3×20 mL) and dried (eight hours in the air, 16 hours under nitrogen) to give 4.07 g (90.6%, corrected for 0.1 molar eq. water), HPLC HI=99.76%.

Elemental Analysis for $C_{20}H_{18}N_5O_2Cl$ (395.85)

Calc'd: C 60.68; H 4.58; N 17.69; Cl 8.96;

Found: C 60.65; H 4.64; N 17.59; Cl 8.90.

What is claimed is:

1. A process for the preparation of compounds of the formula

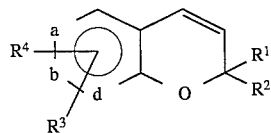

I where a, b, and d are all carbon atoms or one of a, b and c is a nitrogen atom or -NO- and the others are carbon atoms;

$R^1$ and $R^2$ are independently hydrogen, alkyl or arylalkyl, or $R^1$ and $R^2$ taken together with the carbon atom to which they are attached form a 5- to 7-membered carbocyclic ring;

$R^3$ is hydrogen, alkyl, haloalkyl, alkenyl, alkynyl, cycloalkyl, arylalkyl, cycloalkylalkyl, -CN, -$NO_2$, -COR, -COOR, -CONHR, -CONRR', -$CF_3$, S-alkyl, -SOalkyl, -$SO_2$alkyl,

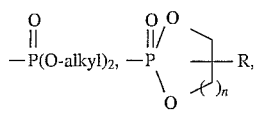

halogen, amino, substituted amino, -OH, -O-alkyl, -OCF$_3$, -OCH$_2$CF$_3$, -OCOalkyl, -OCONRalkyl, -NRCOalkyl, -NRCOOalkyl or -NRCONRR' wherein R and R' in the above groups is independently hydrogen, alkyl, haloalkyl, aryl, arylalkyl, cycloalkyl, or (cycloalkyl)alkyl;

R$^4$ is hydrogen, alkyl, -OH, -O-alkyl, amino, substituted amino, -NHCOR, -CN or -NO$_2$; and n is an integer of 1 to 3; consisting essentially of the step of condensation of a phenol of formula

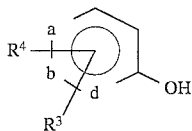

II with an acetal of formula

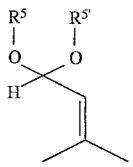

III where R$^5$ and R$^{5'}$ are the same alkyl group or can together form a dioxolane ring in the presence of a catalytic amount of a tertiary amine selected from quinoline, N-methylmorpholine, 4-dimethylaminopyridine, 1,4-diazabicyclo[2.2.2]octane, 1,8-diazabicyclo[5.4.0]undec-7-ene, tributylamine, picoline, lutidine or pyridine in an inert organic solvent selected from toluene or xylene to form compounds of formula I.

2. The process as recited in claim 1 wherein the tertiary amine is pyridine or 3-picoline.

3. The process as recited in claim 1 wherein the reaction is run at a temperature between about 90° C. to about 150° C.

4. A process for the preparation of compounds of formula

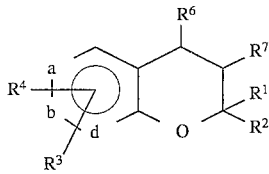

V where a, b, and d are all carbon atoms or one of a, b and c is a nitrogen atom or -NO- and the others are carbon atoms;

R$^1$ and R$^2$ are independently hydrogen, alkyl or arylalkyl, or, R$^1$ and R$^2$ taken together with the carbon atom to which they are attached form a 5- to 7-membered carbocyclic ring;

R$^3$ is hydrogen, alkyl, haloalkyl, alkenyl, alkynyl, cycloalkyl, arylalkyl, cycloalkylalkyl, -CN, -NO$_2$, -COR, -COOR, -CONHR, -CONRR', -CF$_3$, S-alkyl, -SOalkyl, -SO$_2$alkyl,

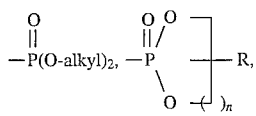

halogen, amino, substituted amino, -OH, -O-alkyl, -OCF$_3$, -OCH$_2$CF$_3$, -OCOalkyl, -OCONRalkyl, -NRCOalkyl, -NRCOOalkyl or -NRCONRR' wherein R and R' in each of the above groups is independently hydrogen, alkyl, haloalkyl, aryl, arylalkyl, cycloalkyl, or (cycloalkyl)alkyl;

R$^4$ is hydrogen, alkyl, -OH, -O-alkyl, amino, substituted amino, -NHCOR, -CN or -NO$_2$;

R$^6$ is

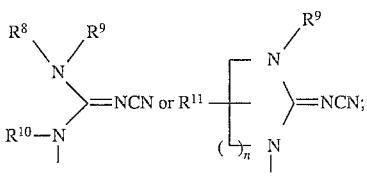

R$^7$ is hydrogen, hydroxy, $$-\underset{\underset{O}{\|}}{O}CCH_3;$$

R$^8$ and R$^9$ are independently hydrogen, alkyl, alkenyl, aryl, (heterocyclo)alkyl, heterocyclo, arylalkyl, cycloalkyl, (cycloalkyl)alkyl or substituted alkyl wherein the substituents are alkoxy, alkylthio and substituted amino; or R$^8$ and R$^9$ taken together with the nitrogen atom to which they are attached form 1-pyrrolidinyl, 1-piperidinyl, 1-acepinyl, 4-morpholinyl, 4-thiamorpholinyl, 1-piperazinyl, 4-alkyl-1-piperazinyl or 4-arylalkyl-1-piperazinyl, wherein each of the so-formed groups can be substituted with alkyl, alkoxy, alkylthio, halogen or trifluoromethyl; and R$^{10}$ and R$^{11}$ are independently hydrogen, alkyl, alkenyl, aryl, arylalkyl, cycloalkyl or (cycloalkyl)alkyl; or R$^{11}$ can be an aryl group fused to 2 carbon atoms of the cyanoguanidine ring portion; and n is an integer of 1 to 3; comprising the steps of (A) preparing a compound of the formula

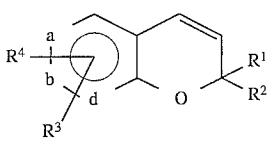

I by the step consisting essentially of condensation of a phenol of formula

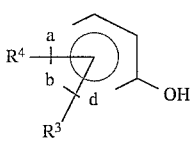

II with an acetal of formula

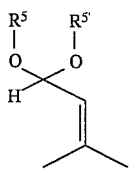

III where $R^5$ and $R^{5'}$ are the same alkyl group or can together form a dioxolane ring in the presence of a catalytic amount of a tertiary amine selected from quinoline, N-methylmorpholine, 4-dimethylaminopyridine, 1,4-diazabicyclo[2.2.2]octane, 1,8-diazabicyclo[5.4.0]undec-7-ene, tributylamine, picoline, lutidine or pyridine in an inert organic solvent selected from toluene or xylene to form compounds of formula I; and (B) converting said compound of the formula I prepared in step (A) to said compound of formula V.

5. The process as recited in claim 4 wherein a compound of the formula

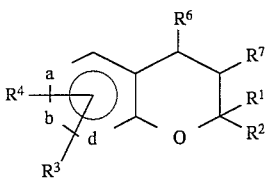

V where $R^6$ is

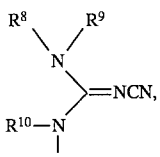

and $R^8$ is mono- or di-substituted phenyl is prepared.

* * * * *